(12) United States Patent
Shibahara

(10) Patent No.: US 8,383,057 B2
(45) Date of Patent: Feb. 26, 2013

(54) PROBE ARRAY SUBSTRATE AND METHOD FOR PRODUCING THE SAME, AND PROBE ARRAY AND METHOD FOR PRODUCING THE SAME

(75) Inventor: Teruhisa Shibahara, Machida (JP)

(73) Assignee: Murata Manufacturing Co., Ltd., Nagaokakyo-Shi, Kyoto-fu (JP)

( * ) Notice: Subject to any disclaimer, the term of this patent is extended or adjusted under 35 U.S.C. 154(b) by 0 days.

(21) Appl. No.: 12/779,276

(22) Filed: May 13, 2010

(65) Prior Publication Data

US 2010/0216668 A1 Aug. 26, 2010

Related U.S. Application Data

(63) Continuation of application No. PCT/JP2008/066705, filed on Sep. 17, 2008.

(30) Foreign Application Priority Data

Nov. 22, 2007 (JP) .................................. 2007-302573

(51) Int. Cl.
*G01N 33/00* (2006.01)
(52) U.S. Cl. ........ 422/408; 422/401; 422/402; 422/534; 435/420; 435/288.4; 435/287.2; 506/39; 506/32
(58) Field of Classification Search .................. 422/57, 422/68.1; 506/35, 38, 39; 435/174, 176, 435/287.2, 288.4, 305.1, 305.2; 264/40.1; 850/63; 977/888; 216/2, 99
See application file for complete search history.

(56) References Cited

U.S. PATENT DOCUMENTS

| | | | |
|---|---|---|---|
| 6,340,589 B1 | 1/2002 | Turner et al. | |
| 6,528,302 B2 | 3/2003 | Turner et al. | |
| 6,716,629 B2 * | 4/2004 | Hess et al. | 435/420 |
| 7,214,353 B2 * | 5/2007 | Feuer et al. | 422/261 |
| 7,713,692 B2 * | 5/2010 | Kawaguchi | 435/6 |
| 2002/0187564 A1 * | 12/2002 | Chow et al. | 436/518 |
| 2003/0180191 A1 | 9/2003 | Suzuki et al. | |
| 2004/0048361 A1 * | 3/2004 | Isobe et al. | 435/287.2 |
| 2004/0142491 A1 * | 7/2004 | Indermuhle et al. | 436/514 |
| 2008/0261830 A1 * | 10/2008 | Shibahara | 506/13 |
| 2009/0042734 A1 | 2/2009 | Yoshida et al. | |

FOREIGN PATENT DOCUMENTS

| | | |
|---|---|---|
| JP | 2001-343386 | 12/2001 |
| JP | 2003-329679 A | 11/2003 |
| JP | 2004-004076 A1 | 1/2004 |
| JP | 2004-045055 A1 | 2/2004 |
| JP | 2004-045179 A | 2/2004 |
| JP | 2006-133077 A | 5/2006 |

(Continued)

OTHER PUBLICATIONS

PCT/JP2008/066705 International Search Report dated Jun. 10, 2008.
PCT/JP2008/066705 Written Opinion dated Jun. 10, 2008.
Japanese Office Action issued Apr. 10, 2012 for application No. JP 2009-542499 (with English translation).

*Primary Examiner* — Sally Merkling
(74) *Attorney, Agent, or Firm* — Dickstein Shapiro LLP

(57) ABSTRACT

A probe array substrate suitable for forming a probe array that has high packing density, that can hold sufficient amounts of probe molecules, and that has little variation in the amounts of probe molecules. A plurality of arrayed probe-holding portions are defined by recesses, and isolating grooves are formed between the adjacent probe-holding portions to prevent probe solutions introduced into the probe-holding portions from spreading to adjacent probe-holding portions. Inner surfaces of the probe-holding portions are made hydrophilic, whereas inner surfaces of the isolating grooves are made hydrophobic. Liquid-introducing protrusions are formed in the probe-holding portions.

19 Claims, 12 Drawing Sheets

FOREIGN PATENT DOCUMENTS

| | | |
|---|---|---|
| WO | WO-02-25289 | 3/2002 |
| WO | WO-2006/101229 A1 | 9/2006 |
| WO | WO-2007-080761 | 7/2007 |
| WO | WO2007080761 * | 7/2007 |

* cited by examiner

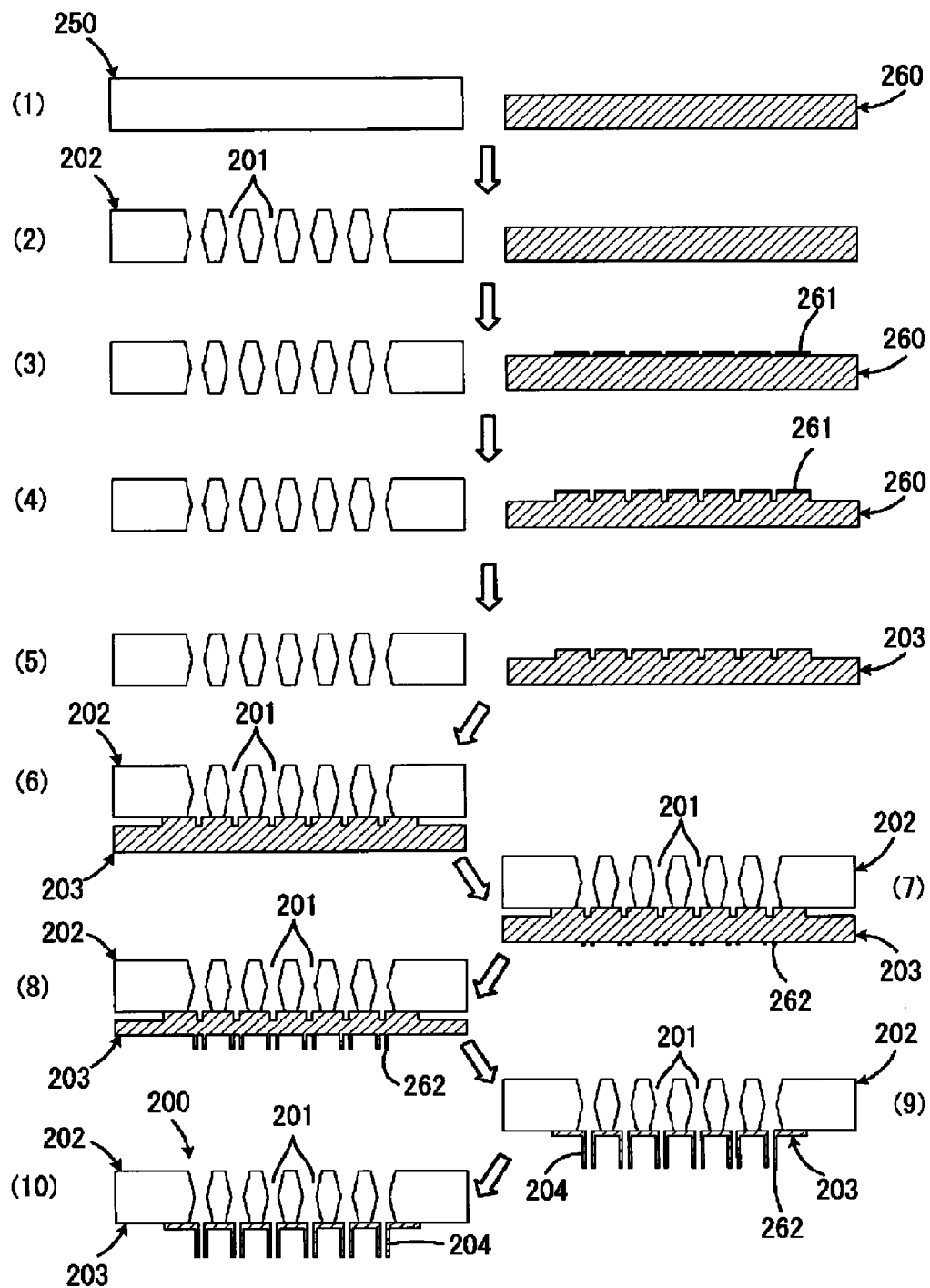

US 8,383,057 B2

PROBE ARRAY SUBSTRATE AND METHOD FOR PRODUCING THE SAME, AND PROBE ARRAY AND METHOD FOR PRODUCING THE SAME

CROSS REFERENCE TO RELATED APPLICATIONS

The present application is a continuation of International Application No. PCT/JP2008/066705, filed Sep. 17, 2008, which claims priority to Japanese Patent Application No. JP2007-302573, filed Nov. 22, 2007, the entire contents of each of these applications being incorporated herein by reference in their entirety.

FIELD OF THE INVENTION

The present invention relates to probe array substrates for use in the field of chemistry or biochemistry and methods for producing probe array substrates, and also to probe arrays formed using probe array substrates and methods for producing probe arrays.

BACKGROUND OF THE INVENTION

DNA chips have attracted attention as a tool, for example, for simultaneous genetic diagnosis for many items, simultaneous examination of many types of mRNAs for expression level, and simultaneous examination for many single nucleotide polymorphisms (SNPs). DNA chips, also called DNA microarrays, are probe arrays using known DNAs that hybridize with target DNA molecules or RNA molecules as probes, having a plurality of types of probes held on a plurality of periodically arranged probe-holding portions.

In addition, antigen chips and antibody chips have attracted attention as a tool used for simultaneous examination for the presence or absence of many types of antigens or antibodies. Antigen chips are probe arrays using known antigens that bind to target antibody molecules as probes, having a plurality of types of probes held on a plurality of periodically arranged probe-holding portions. Antibody chips are probe arrays using known antibody molecules that bind to target antigens as probes, having a plurality of types of probes held on a plurality of periodically arranged probe-holding portions.

As a common method for producing a probe array, a method is known in which probe solutions (solutions containing probe molecules) are deposited in a dot pattern on a substrate such as a glass slide (hereinafter referred to as "spotting") so that the probe molecules chemically bond to the surface of the substrate, thereby arranging probe spots on the surface of the substrate. Specifically, known spotting methods include a method in which a probe solution is ejected onto a substrate using an injection needle or a micropipette or by inkjet ejection and a method in which a probe solution placed at a needle tip is brought into contact with a substrate.

For the method using spotting, for example, Japanese Unexamined Patent Application Publication No. 2004-45055 (Patent Document 1) discloses a micropipette used for densely arranging droplets of extremely small volume. In addition, for example, Japanese Unexamined Patent Application Publication No. 2004-4076 (Patent Document 2) discloses a method for producing an array substrate configured to allow droplets supplied from a micropipette to be efficiently arranged thereon and to prevent the droplets from being mixed.

A probe array is preferably capable of having as many types of probes (probes holding different types of probe molecules or probes themselves) as possible arranged within a specific area. That is, a probe array having a higher packing density (number of spots arranged per unit area) is preferred. There is a problem, however, in that a probe array having a sufficiently high packing density cannot be produced because the spot area increases as the spotted probe solutions spread over the substrate.

In addition, the probe spots on the probe array need to hold sufficient amounts of probe molecules. If the probes hold insufficient amounts of probe molecules, it is difficult to detect target molecules because insufficient amounts of target molecules are bound to or hybridized with the probes. However, if the packing density of the probe array is increased, the spot area is decreased, and consequently the probe spots tend to contain insufficient amounts of probe molecules, often leading to the problem of insufficient detection sensitivity for target molecules.

In addition, the amounts of probe molecules held in the probes on the probe array are preferably constant and vary little. If the amounts of probe molecules held in the probes vary, the amounts of target molecules bound to or hybridized with the probes vary even through the concentrations of the target molecules in the solution under examination remain the same, thus leading to the problem that the concentrations of the target molecules in the solution under examination cannot be accurately determined because of varying signal strengths. The method using spotting, however, has a problem in that the amounts of probe molecules held at the probe spots tend to vary because the amounts of probe solutions spotted on the substrate tend to vary.

The above problems are particularly serious in the production of a probe array having high packing density. This is because extremely small amounts of probe solutions are spotted in the production of a probe array having high packing density and therefore slight variations in the amounts of probe solutions are more influential.

[Patent Document 1] Japanese Unexamined Patent Application Publication No. 2004-45055

[Patent Document 2] Japanese Unexamined Patent Application Publication No. 2004-4076

SUMMARY OF THE INVENTION

Accordingly, an object of the present invention is to provide a probe array having high packing density and a method for producing the probe array, and also to provide a probe array substrate suitable for achieving such a probe array and a method for producing the probe array substrate.

Another object of the present invention is to provide a probe array capable of holding sufficient amounts of probe molecules in individual probe-holding portions at a higher packing density and a method for producing the probe array, and also to provide a probe array substrate suitable for achieving such a probe array and a method for producing the probe array substrate.

A further object of the present invention is to provide a probe array having little variation in the amounts of probe solutions held in individual probe-holding portions and therefore little variation in the amounts of probe molecules held in the individual probe-holding portions and a method for producing the probe array, and also to provide a probe array substrate suitable for achieving such a probe array and a method for producing the probe array substrate.

The present invention is first directed to a probe array substrate having a main surface and a plurality of probe-holding portions arranged along the main surface, and to solve the technical problems described above, is characterized in that the individual probe-holding portions are defined by recesses in the main surface and that descending wall surfaces descending from the main surface in a substantially perpendicular direction are formed between the adjacent probe-holding portions.

In the probe array substrate according to the present invention, preferably, isolating grooves having openings in the main surface are formed between the adjacent probe-holding portions, and the descending wall surfaces described above are defined by side surfaces of the isolating grooves.

In addition, preferably, inner surfaces defining the probe-holding portions are hydrophilic, and the descending wall surfaces are hydrophobic. The terms "hydrophilic" and "hydrophobic" are usually used as terms referring to the presence or absence of wettability (affinity) to water; in the present case, a state of high wettability to probe solutions is expressed as being "hydrophilic", and a state of low wettability to probe solutions is expressed as being "hydrophobic", irrespective of whether or not the probe solutions are aqueous solutions.

In addition, preferably, liquid-introducing protrusions are formed in the probe-holding portions, and more preferably, the liquid-introducing protrusions have guide grooves for smoothly introducing probe solutions into the probe-holding portions.

The present invention is further directed to a method for producing a probe array substrate plate-shaped as a whole and, as described above, having a main surface and a plurality of probe-holding portions arranged along the main surface.

The method for producing a probe array substrate according to the present invention is characterized by including the steps of preparing a plate-shaped material substrate to be the probe array substrate, forming recesses in the main surface of the material substrate to form the probe-holding portions, forming isolating grooves having openings in the main surface between the adjacent probe-holding portions of the material substrate, and making inner surfaces of the isolating grooves hydrophobic by pouring a liquid capable of making the surfaces of the isolating grooves hydrophobic into the isolating grooves.

In the method for producing a probe array substrate according to the present invention, preferably, the step of forming the recesses and the step of forming the isolating grooves are simultaneously carried out. More preferably, the material substrate is formed of silicon, and the step of forming the recesses and the step of forming the isolating grooves include a step of forming the recesses and the isolating grooves by dry etching.

In a more specific embodiment, the material substrate is a monocrystalline silicon substrate whose main surface is a (110) crystal plane and is designed so that inner surfaces defining the recesses and the inner surfaces defining the isolating grooves are (111) crystal planes, and the step of forming the recesses and the step of forming the isolating grooves include a step of forming the recesses and the isolating grooves by wet etching with an alkaline liquid.

The present invention is further directed to a probe array including the above probe array substrate according to the present invention and probe molecules held in the individual probe-holding portions formed on the probe array substrate.

The present invention is further directed to a method for producing a probe array using the probe array substrate according to the present invention.

To implement the method for producing a probe array according to the present invention, the probe array substrate, as described above, having the liquid-introducing protrusions formed in the probe-holding portions is prepared. Further implemented are a step of preparing nozzles charged with probe solutions and a step of guiding the probe solutions into the probe-holding portions of the probe array substrate by bringing the nozzles close to the liquid-introducing protrusions formed in the probe-holding portions so that the probe solutions come into contact with the liquid-introducing protrusions.

In the method for producing a probe array according to the present invention, preferably, the following relationship holds:

$$I < [D \times \cosh\{\operatorname{arcsinh}(1/\tan \theta 2)\}]/[2 \times \cosh\{\operatorname{arcsinh}(\tan \theta 3)\}]$$

wherein
D is the outer diameter of the nozzles;
I is the distance between inner side surfaces of the probe-holding portions and the liquid-introducing protrusions;
θ2 is the wetting angle between the main surface of the probe array substrate and the probe solutions around the probe-holding portions; and
θ3 is the wetting angle between peripheral surfaces of the nozzles and the probe solutions.

In addition, in the method for producing a probe array according to the present invention, preferably, the following relationship holds:

$$N > D \times [\operatorname{arccosh}\{(2E/D) \times \cosh(\phi)\} - \phi]/[2 \times \cosh(\phi)]$$

wherein
D is the outer diameter of the nozzles;
N is the length of the nozzles;
E is the distance from the centers of the liquid-introducing protrusions to the descending wall surfaces;
θ3 is the wetting angle between peripheral surfaces of the nozzles and the probe solutions; and
φ is defined as $\phi = \operatorname{arcsinh}(\tan \theta 3)$.

In the method for producing a probe array according to the present invention, preferably, peripheral surfaces of the nozzles are at least partially hydrophobic.

In addition, preferably, the method for producing a probe array according to the present invention further includes a step of preparing a feeder having the nozzles arranged thereon, and the step of guiding the probe solutions into the probe-holding portions includes a step of simultaneously introducing the probe solutions into the probe-holding portions by bringing the feeder close to the probe array substrate so that the probe solutions come into contact with the liquid-introducing protrusions.

According to the present invention, because the probe-holding portions are defined by recesses and the descending wall surfaces are formed between the adjacent probe-holding portions, the probe solutions to be introduced into the probe-holding portions are inhibited from spreading over the main surface, so that the packing density of the probes on the probe array can be increased.

According to the present invention, additionally, because the probe-holding portions are defined by recesses, relatively large amounts of probe solutions can be introduced into the probe-holding portions, and the probe molecules can also be held on the inner side surfaces of the recesses. Accordingly, even if the packing density is increased, as described above, the individual probe-holding portions can contain sufficient amounts of probe molecules. This eliminates the problem of insufficient detection sensitivity for target molecules due to insufficient amounts of probe molecules.

According to the present invention, additionally, variations in the amounts of probe solutions introduced into the probe-holding portions are reduced because they are strictly controlled by the shape and volume of the probe-holding portions defined by recesses, so that manufacturing variations in the amounts of probe molecules held in the probe-holding portions are reduced. As a result, manufacturing variations in the sensitivity of the probe array can be reduced.

BRIEF DESCRIPTION OF THE DRAWINGS

FIG. 7 is a set of end views of the feeder 200, taken along a particular cross section, for illustrating a process executed for producing the feeder 200 shown in FIG. 5.

Figure 1:
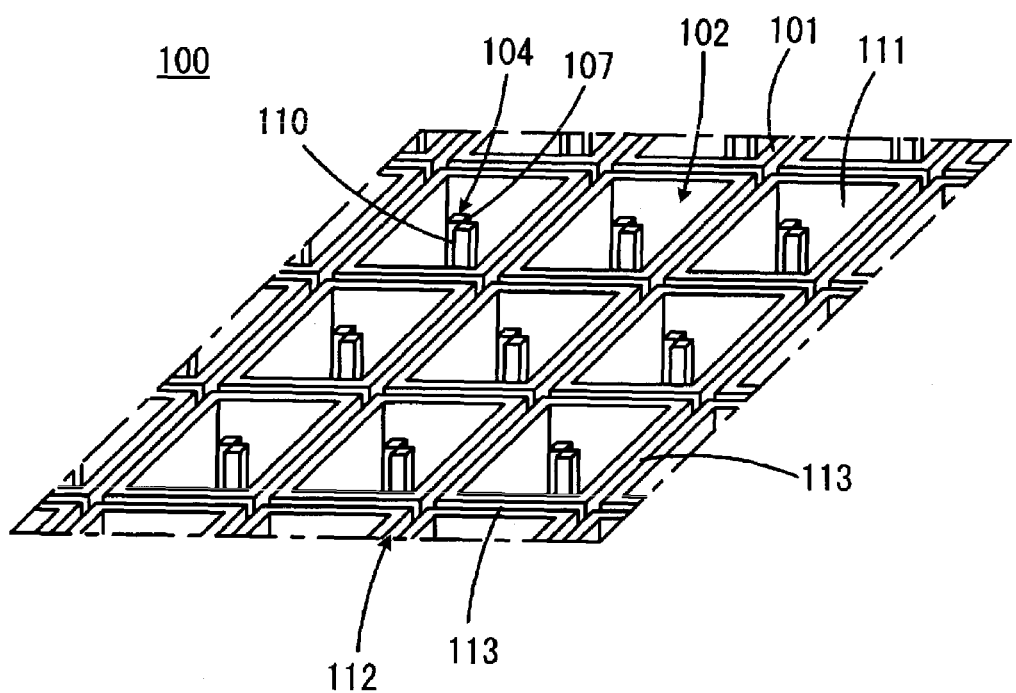
FIG. 1 is a perspective view showing part of a probe array substrate 100 according to a first embodiment of the present invention.

REFERENCE NUMERALS 100 probe array substrate
101 main surface
102 probe-holding portion
103 bottom surface
104, 151, 152, 153 liquid-introducing protrusion
107, 110, 156, 159, 162, 165, 168, 172 guide groove
111 inner side surface
112 isolating groove
113 descending wall surface
120 material substrate
121 resist pattern
122 hydrophobing agent
200 feeder
204 nozzle
210 aqueous probe solution

DETAILED DESCRIPTION OF THE INVENTION

Figure 2:
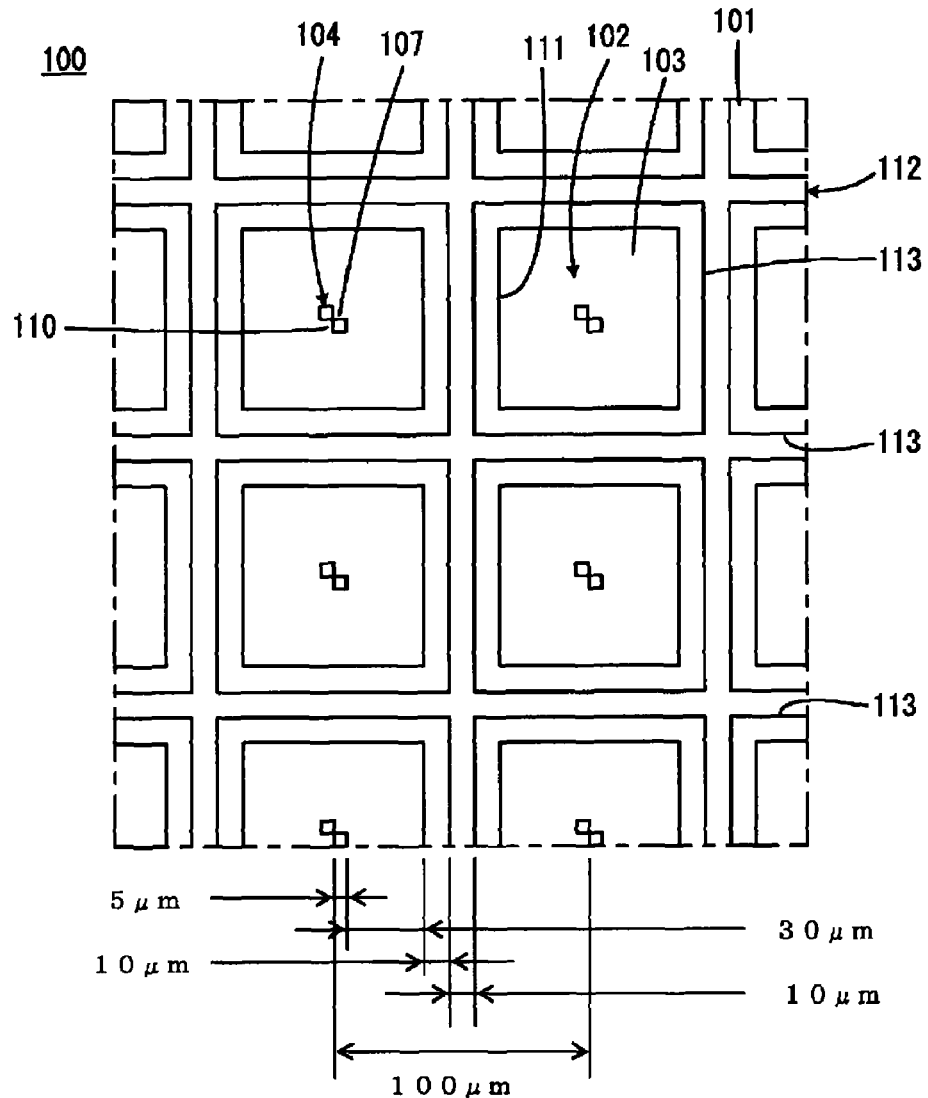
FIG. 2 is a top view showing part of the probe array substrate 100 shown in FIG. 1.

FIG. 1 is a perspective view showing part of a probe array substrate 100 according to a first embodiment of the present invention. FIG. 2 is a top view showing part of the probe array substrate 100 shown in FIG. 1.

Referring to FIGS. 1 and 2, the probe array substrate 100 has a main surface 101 and is plate-shaped as a whole. The probe array substrate 100 has a plurality of probe-holding portions 102 arranged in rows and columns along the main surface 101. The probe-holding portions 102 have an array pitch of, for example, 100 as shown in FIG. 2. The individual probe-holding portions 102 are defined by recesses in the main surface 101. In the embodiment shown, the individual probe-holding portions 102 are defined by recesses having bottom surfaces 103 at a level lower than the main surface 101. In another embodiment, the probe-holding portions can be defined by through-holes having no bottom surfaces.

Figure 3:
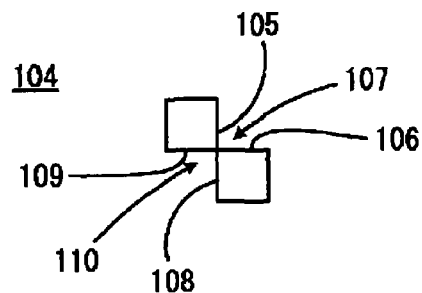
FIG. 3 is an enlarged top view of a liquid-introducing protrusion 104 formed on a bottom surface 103 of a probe-holding portion 102 on the probe array substrate 100 shown in FIGS. 1 and 2.

Liquid-introducing protrusions 104 are formed in the probe-holding portions 102. In this embodiment, the liquid-introducing protrusions 104 are positioned in the centers of the bottom surfaces 103 of the probe-holding portions 102. FIG. 3 shows an enlarged view of a liquid-introducing protrusion 104. The liquid-introducing protrusion 104 has such a shape that two square prisms are arranged diagonally with a ridge of one square prism in contact with a ridge of the other prism. The sides of the squares defining the cross sections of the square prisms have a length of, for example, 5 μm, as shown in FIG. 2.

The liquid-introducing protrusion 104 having the shape described above, as clearly shown in FIG. 3, has a guide groove 107, having an L-shaped cross section defined by surfaces 105 and 106, and a guide groove 110, having an L-shaped cross section defined by surfaces 108 and 109, that are formed so as to face each other diagonally. As shown in FIG. 2, the distance between the liquid-introducing protrusions 104 and inner side surfaces 111 of the probe-holding portions 102 is, for example, 30 μm.

The functions of the liquid-introducing protrusions 104 and the guide grooves 107 and 110 described above will be described later.

Isolating grooves 112 having openings in the main surface 101 are formed between the adjacent probe-holding portions 102. The isolating grooves 112 extend in a grid pattern in the main surface 101 of the probe array substrate 100. The isolating grooves 112 prevent probe solutions to be introduced into the probe-holding portions 102 from spreading over the main surface 101. The above function of the isolating grooves 112 is implemented by side surfaces of the isolating grooves 112, that is, descending wall surfaces 113 descending from the main surface 101 in a substantially perpendicular direction, as described in detail later. In this regard, it is important to form the descending wall surfaces 113; the isolating grooves 112 may be replaced by, for example, slits extending through the probe array substrate 100 in the thickness direction.

As shown in FIG. 2, the isolating grooves 112 have a width of, for example, 10 μm, and the distance from the inner wall surfaces 111 of the probe-holding portions 102 to the isolating grooves 112 is, for example, 10 μm. In addition, the probe-holding portions 102 and the isolating grooves 112 both have a depth of, for example, 100 μm and are formed by, for example, etching a material substrate of monocrystalline silicon having a thickness of 500 μm.

Figure 4:
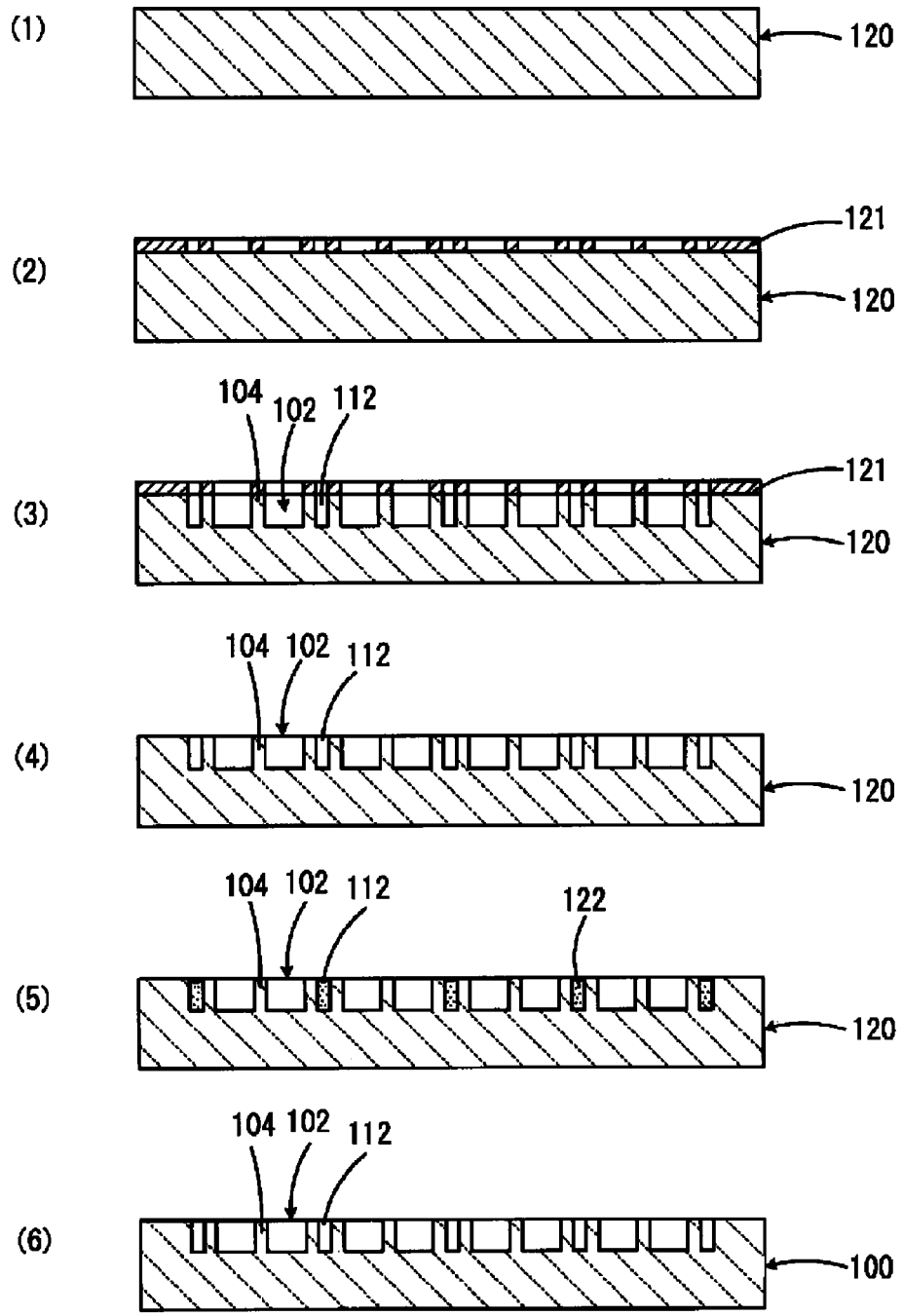
FIG. 4 is a set of sectional views showing a process executed for producing the probe array substrate 100 shown in FIGS. 1 and 2.

Next, a method for producing the probe array substrate 100 will be described. FIG. 4 shows a typical process executed for producing the probe array substrate 100.

First, as shown in FIG. 4(1), a plate-shaped material substrate 120 to be the probe array substrate 100 is prepared. The material substrate 120 is formed of, for example, a monocrystalline silicon substrate having a thickness of 500 μm.

Next, as shown in FIG. 4(2), a resist pattern 121 is formed on a surface of the material substrate 120 by photolithography. In relation to the probe array substrate 100 shown in FIG. 2, the resist pattern 121 is formed so as to cover the portions to be the liquid-introducing protrusions 104 and the portions other than the portions to be the probe-holding portions 102 and the isolating grooves 112.

Next, as shown in FIG. 4(3), the material substrate 120 is etched to a depth of, for example, 100 μm by dry etching using the resist pattern 121 as a mask. For dry etching, for example, inductive coupling plasma reactive ion etching (ICP-RIE) is advantageously employed, and the etching is performed with a plasma of a fluorinated gas such as $CF_4$ or $SF_6$. After this step, the recesses to be the probe-holding portions 102 are formed on the material substrate 120, and the shapes of the liquid-introducing protrusions 104 and the isolating grooves 112 are also defined thereon.

Next, as shown in FIG. 4(4), the material substrate 120 is cleaned with a mixed solution of sulfuric acid and aqueous hydrogen peroxide to remove the resist pattern 121 and organic contaminants from the surface. The material substrate 120 is then cleaned with a mixed solution of aqueous ammonia and aqueous hydrogen peroxide to remove, for example, dust from the surface and to form an oxide film, followed by rinsing and drying. After this step, the entire surface of the material substrate 120 is made hydrophilic by the oxide film.

Next, as shown in FIG. 4(5), a hydrophobing agent 122 is poured into the isolating grooves 112 of the material substrate 120 and is left standing at room temperature for about 60 minutes. The hydrophobing agent 122 is a liquid capable of making the surfaces of the isolating grooves 112 hydrophobic, and as the hydrophobing agent 122, for example, a solution of a silane coupling agent having a hydrophobic group such as an alkyl group, a halogenated alkyl group, or a fluoro group is used.

Afterwards, as shown in FIG. 4(6), the hydrophobing agent 122 is sucked up and is dried by leaving it standing at an appropriate temperature. This procedure makes the inner surfaces of the isolating grooves 112, including the descending wall surfaces 113, hydrophobic.

Thus, the probe array substrate 100 is completed.

Instead of the silane coupling agent solution described above, the hydrophobing agent 122 used may be a liquid, such as silicone oil, that is hydrophobic and does not volatilize. If the hydrophobic liquid is poured into the isolating grooves 112 and an excess of the liquid is sucked up, the hydrophobic liquid remaining on the inner surfaces of the isolating grooves 112 makes the surfaces of the isolating grooves 112 hydrophobic.

Subsequently, maleimide groups are introduced to the outermost surfaces of the probe-holding portions 102 of the probe array substrate 100 by the following procedure. That is, an aqueous solution of an aminosilane such as N-β-(aminoethyl)-γ-aminopropyltrimethoxysilane is prepared, and the probe array substrate 100 is dipped therein. The probe array substrate 100 is then removed from the aqueous aminosilane solution, is dried, and is heated to about 120° C. With the above procedure, amino groups are introduced to the outermost surface of the probe array substrate 100. The amino groups on the outermost surface of the probe array substrate 100 are then changed to maleimide groups using a reagent containing N-(6-maleimidocaproyloxy)succinimide.

The probe array substrate 100 remains hydrophilic after the introduction of maleimide groups to the outermost surface of the probe array substrate 100, as described above. The step of introducing maleimide groups may be performed before or after the treatment for making the inner surfaces of the isolating grooves 112 hydrophobic.

According to the method for producing the probe array substrate 100 described above, the inner surfaces of the isolating grooves 112 can be made hydrophobic simply by pouring the hydrophobing agent 122 into the isolating grooves 112, so that the step of making the descending wall surfaces 113, defined by the side surfaces of the isolating grooves 112, hydrophobic can be easily performed at low cost.

In the method for producing the probe array substrate 100 described above, additionally, the probe-holding portions 102 and the isolating grooves 112 are formed on the material substrate 120 of monocrystalline silicon by dry etching. With this method, fine, high-aspect probe-holding portions 102 and isolating grooves 112 can be formed by a single etching step. The term "high aspect" herein means that the depth of etching is large relative to the width of the openings. Dry etching allows the material substrate 120 of monocrystalline silicon to be processed to an aspect ratio (the depth of etching divided by the width of the openings) exceeding 20.

Instead of the method using dry etching, if a monocrystalline silicon substrate whose main surface is a (110) crystal plane is used as the material substrate 120 and is designed so that the inner surfaces defining the recesses to be the probe-holding portions 102 having the liquid-introducing protrusions 104 and the inner surfaces defining the isolating grooves 112 are (111) crystal planes, high-aspect-ratio probe-holding portions 102 and isolating grooves 112 having an aspect ratio exceeding 20 can be formed by wet etching with an aqueous alkaline solution such as an aqueous potassium hydroxide solution or an aqueous TMAH solution.

As compared to the method using dry etching, the method using wet etching has the disadvantage of limitations to the designs of the probe-holding portions 102 and the isolating grooves 112, but has the advantage of low cost because expensive vacuum equipment is not required for etching.

However, if wet etching with an alkaline liquid is employed, a photoresist pattern cannot be used as a mask. Therefore, for example, it is necessary before wet etching to form an oxide film having a thickness of about 1 μm on the surface of the material substrate 120 by a method such as steam oxidation and pattern the oxide film to use it as a mask for wet etching.

Next, a method for producing a probe array using the probe array substrate 100 described above, more specifically, a method for producing a DNA chip having a plurality of types of probe DNAs arranged thereon, will be described.

Figure 5:
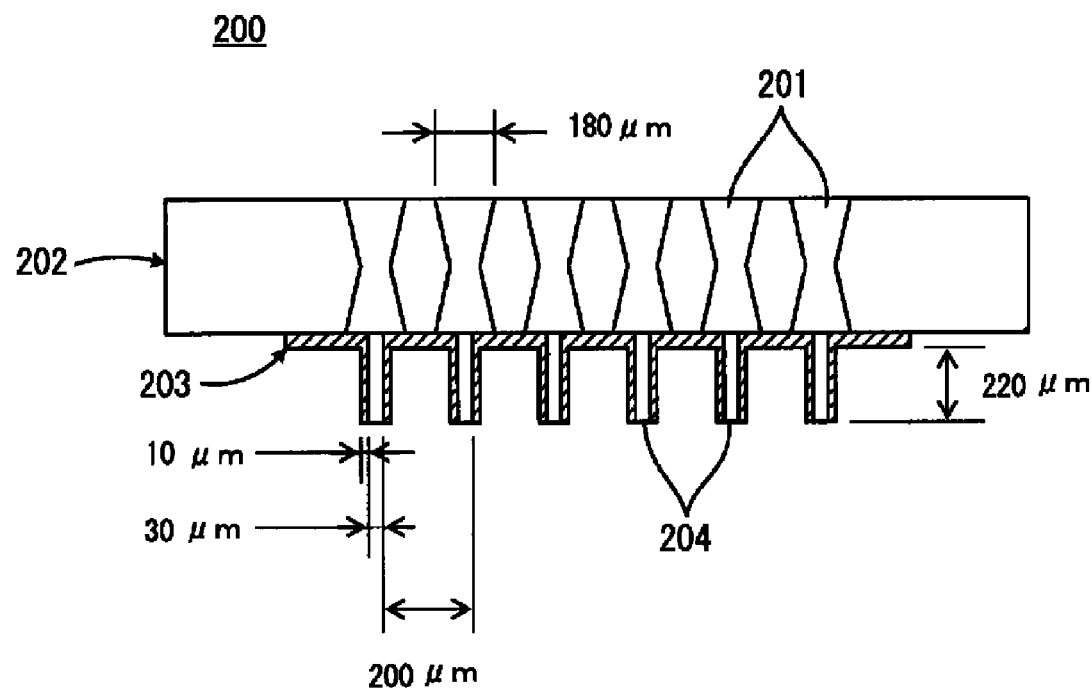
FIG. 5 is a sectional view showing a feeder 200 advantageously used in combination with the probe array substrate 100 shown in FIGS. 1 and 2 to produce a probe array using the probe array substrate 100.

A feeder 200, as shown in FIG. 5, is used in the production of the DNA chip, which serves as the probe array described above. The feeder 200 is composed of, for example, a glass portion 202 having a plurality of through-holes 201 having a diameter of 180 μm and formed at a pitch of 200 μm and a finely processed silicon portion 203. The silicon portion 203 has nozzles 204 communicating with the through-holes 201 formed in the glass portion 202. The nozzles 204 have an inner diameter of, for example, 30 μm, a wall thickness of, for example, 10 μm, and an outer diameter of, for example, 50 μm. In addition, the nozzles 204 have a length of, for example, 220 μm.

Figure 6:
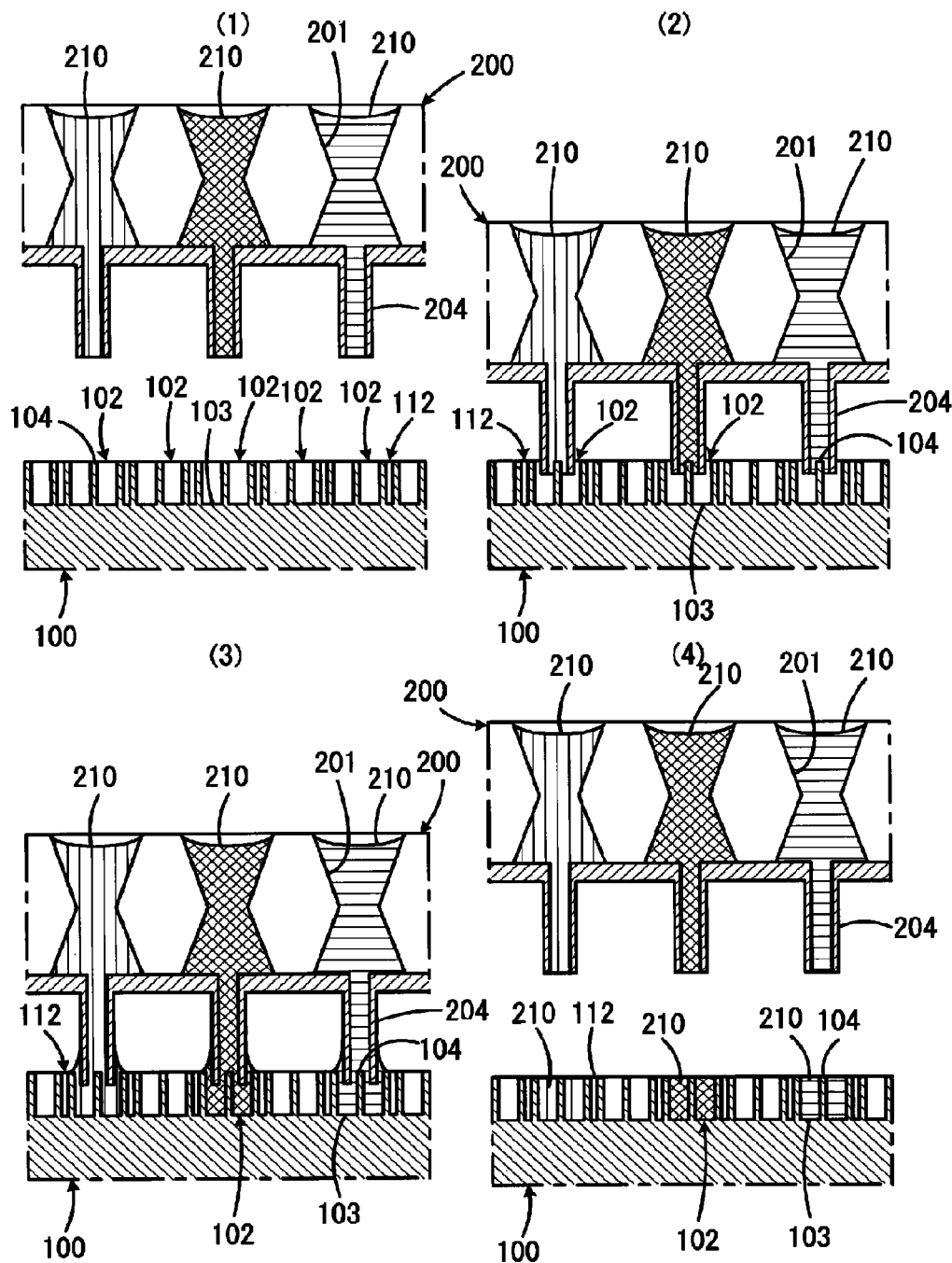
FIG. 6 is a set of sectional views showing a process executed for producing a probe array using the probe array substrate 100 shown in FIGS. 1 and 2 and the feeder 200 shown in FIG. 5.

As shown in FIG. 6(1), the individual through-holes 201 of the feeder 200 are charged with aqueous probe solutions 210 containing probe DNAs. As the aqueous probe solutions 210, a plurality of types of aqueous probe solutions are prepared, each charged into a different through-hole 201. As the probe DNAs contained in the aqueous probe solutions 210, probe DNAs having a thiol group added to the 5'-end thereof are used. The aqueous probe solutions 210 charged in the through-holes 201 do not spontaneously fall off from the nozzles 204 because the through-holes 201 and the nozzles 204 have sufficiently small inner diameters.

To prevent a decrease in the concentration of the aqueous probe solutions 210 as a result of adsorption of the probe DNAs onto the surface of the feeder 200, the surface of the feeder 200 may be washed with the same aqueous probe solutions 210 several times or may be washed with an aqueous solution of bovine serum albumin (BSA) or appropriate DNA fragments for blocking before the through-holes 201 are charged with the aqueous probe solutions 210.

Also prepared, as described above, is the probe array substrate 100 on which the inner surfaces of the isolating grooves 112 are made hydrophobic while maleimide groups are introduced to the outermost surfaces, including the inner surfaces, of the probe-holding portions 102. As shown in FIG. 6(2), the probe array substrate 100 and the feeder 200 are brought close to each other while being aligned. As a result, the individual aqueous probe solutions 210 in the openings of the nozzles 204 are brought into contact with the liquid-introducing protrusions 104 of the probe array substrate 100. At this time, for example, if the tips of the nozzles 204 are brought close to the bottom surfaces 103 of the probe-holding portions 102 to a distance of about 80 μm, the liquid-introducing protrusions 104 are inserted into the nozzles 204 by about 20 μm, so that the aqueous probe solutions 210 reliably come into contact with the liquid-introducing protrusions 104.

Although the detailed operation mechanism will be described later, when the aqueous probe solutions 210 come into contact with the liquid-introducing protrusions 104, as described above, the aqueous probe solutions 210 are introduced and charged into the individual probe-holding portions 102 of the probe array substrate 100, as shown in FIG. 6(3), by a wetting force acting between the aqueous probe solutions 210 and the probe-holding portions 102 of the probe array substrate 100.

Then, as shown in FIG. 6(4), the feeder 200 is moved away, and the probe array substrate 100 is left standing for about one hour. As a result, the thiol groups at the 5'-ends of the probe DNAs chemically bond to the maleimide groups on the outermost surface of the probe array substrate 100, thus allowing the probe DNA molecules, serving as probes, to be held in the probe-holding portions 102 of the probe array substrate 100. After rinsing and drying, the DNA chip is completed.

Whereas the probe DNA molecules and the probe array substrate 100 are bonded together by bonds between maleimide groups and thiol groups in the embodiment described above, other types of bonds such as avidin-biotin bonds may instead be used.

If the probe-holding portions 102 are formed at a pitch of 100 μm on the probe array substrate 100 and the nozzles 204 are formed at a pitch of 200 μm on the feeder 200, the method shown in FIG. 6 cannot be used to charge all probe-holding portions 102 of the probe array substrate 100 with the aqueous probe DNA solutions. However, all probe-holding portions 102 can be charged with different aqueous probe DNA solutions if four feeders 200 charged with different aqueous probe DNA solutions are prepared and are sequentially used to introduce the aqueous probe DNA solutions into the probe array substrate 100.

Instead of the feeder 200, simple nozzles (capillaries) may be used to charge the probe array substrate 100 with the aqueous probe DNA solutions, although this method takes time and cost because the nozzles must be aligned and brought close one by one for all the probe-holding portions 102 of the probe array substrate 100. As shown in FIG. 6, therefore, it is preferable to use the feeder 200 having the nozzles.

In the method for producing a probe array described above, more specifically, in the method for producing a DNA chip, the aqueous probe solutions 210 are introduced and charged into the probe-holding portions 102 of the probe array substrate 100 by a wetting force acting between the probe-holding portions 102 of the probe array substrate 100 and the aqueous probe solutions 210. Accordingly, the amounts of aqueous probe solutions 210 charged are governed by the shape and volume of the probe-holding portions 102.

If the probe array substrate 100 is produced by the method shown in FIG. 4, the shape and volume of the probe-holding portions 102 can be strictly controlled, so that the amounts of aqueous probe solutions 210 spotted can be much more strictly controlled than in a conventional method in which aqueous probe solutions are spotted by inkjet ejection or contact with needle tips. This significantly reduces manufacturing variations in the sensitivity of the probe array produced.

Next, an example of a method for producing the feeder 200 will be described with reference to FIG. 7.

First, as shown in FIG. 7(1), a glass wafer 250 having a thickness of 350 μm and polished on both surfaces and a silicon wafer 260 having a thickness of 250 μm and polished on both surfaces are prepared.

Next, as shown in FIG. 7(2), the through-holes 201 are formed in the glass wafer 250 by sand blasting using a resist pattern formed by photolithography as a mask, so that the glass portion 202 for the feeder 200 is provided. At this time, the through-holes 201 may be formed by processing only one surface of the glass wafer 250 or by processing one surface of the glass wafer 250 to a depth of about 200 μm and then processing the opposite surface.

Next, as shown in FIG. 7(3), a resist pattern 261 is formed on one main surface of the silicon wafer 260 by photolithography.

Next, as shown in FIG. 7(4), the silicon wafer 260 is etched to a depth of about 50 μm by ICP-RIE using the resist pattern 261 as a mask.

Next, the resist pattern 261 is removed from the silicon wafer 260, so that the silicon portion 203 for the feeder 200 is provided, as shown in FIG. 7(5).

Next, as shown in FIG. 7(6), the etched main surface of the silicon portion 203 and one main surface of the glass portion 202 are bonded together by anode coupling with the etched portions of the silicon portion 203 aligned to the through-holes 201 of the glass portion 202. Anode coupling is a technique for bonding silicon and glass by stacking the silicon and the glass, heating the stack to about 300° C. to 500° C., and applying a DC voltage of several hundreds of volts in such a direction that the silicon serves as an anode and the glass serves as a cathode. Anode coupling allows atoms on the outermost silicon surface and atoms on the outermost glass surface to be bonded together, thus forming an airtight junction.

Next, as shown in FIG. 7(7), a resist pattern 262 is formed on the outer main surface of the silicon portion 203 by photolithography.

Next, as sequentially shown in FIGS. 7(8) and 7(9), the silicon portion 203 is etched to form the nozzles 204 by ICP-RIE using the resist pattern 262 as a mask until the etched portions communicate with those formed in the step shown in FIG. 7(4).

Next, the resist pattern 262 is removed from the silicon portion 203, so that the feeder 200 is provided, as shown in FIG. 7(10).

If the probe array substrate 100 according to the present invention is used, probe solutions are prevented from spreading, for example, even if they are spotted in excessive amounts, by the ridges of corners formed by the descending wall surfaces 113, defined by the side surfaces of the isolating grooves 112, and the main surface 101. The reason will be described using FIGS. 8 to 10.

Figure 8A:
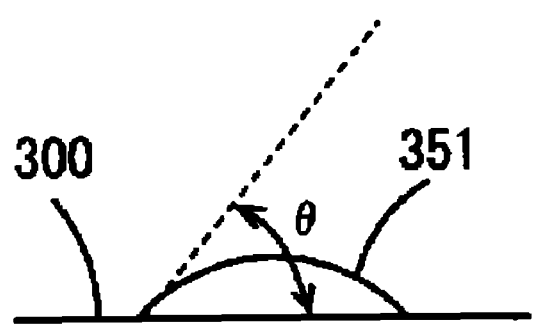
FIGS. 8(a) and 8(b) are a set of diagrams for illustrating an angle θ formed by a liquid surface 351 and a solid surface 300 in a steady state where the liquid is in contact with the solid surface 300.
Figure 8B:
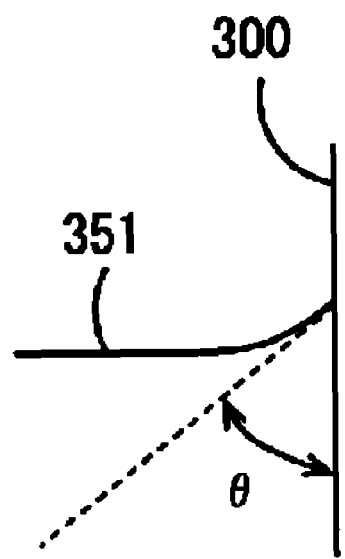

Referring to FIGS. 8(a) and 8(b), when a liquid is in contact with a solid surface 300, the angle θ formed by a liquid surface 351 and the solid surface 300 is a constant value determined by the combination of the liquid and the solid in a steady state unless special circumstances exist. The angle θ is referred to as the wetting angle between the liquid and the solid. The wetting angle is determined by the surface free energy of the solid per unit area, the surface free energy of the liquid per unit area (surface tension), and the interfacial free energy of the interface between the solid and the liquid per unit area, and the fact that the solid surface and the liquid in contact form a constant wetting angle is derived from the principle of minimum free energy.

A smaller wetting angle means that the liquid more easily wets the solid surface, whereas a larger wetting angle means that the liquid less easily wets the solid surface. If the liquid is water or an aqueous solution, the wetting angle is less than 90° C. if the solid surface is hydrophilic and is more than 90° C. if the solid surface is hydrophobic.

The behavior of a droplet at the moment of landing on the solid surface 300 will be described using FIGS. 9(a) and 9(b). The outline of the droplet at the moment of landing is indicated by the dotted line 302 or 303.

Figure 9A:
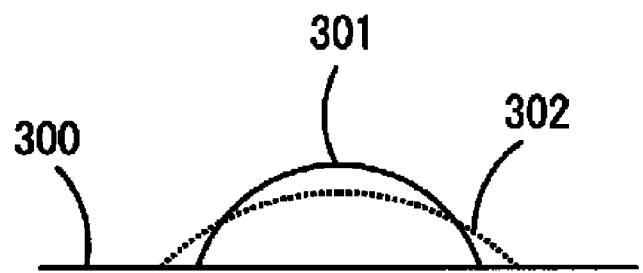
FIGS. 9(a) and 9(b) are a set of diagrams for illustrating the behavior of a droplet at the moment of landing on the solid surface 300.

FIG. 9(a) shows the case where the angle formed by the surface 302 of the droplet at the moment of landing and the solid surface 300 is smaller than the original wetting angle between the solid surface 300 and the droplet. In this case, the droplet is rounded so as to recede from the solid surface 300, finally becoming the shape defined by the original wetting angle (solid line 301).

Figure 9B:
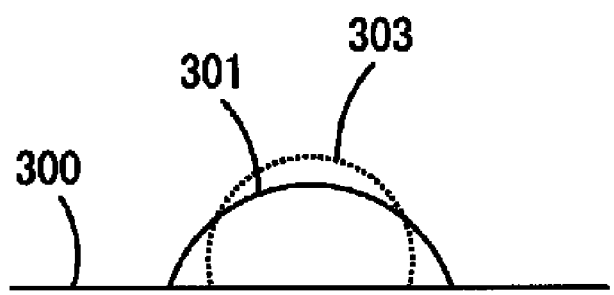

On the other hand, FIG. 9(b) shows the case where the angle formed by the surface 303 of the droplet at the moment of landing and the solid surface 300 is larger than the original wetting angle between the solid surface 300 and the droplet. In this case, the droplet spreads over the solid surface 300, finally becoming the shape defined by the original wetting angle (solid line 301).

Figure 10A:
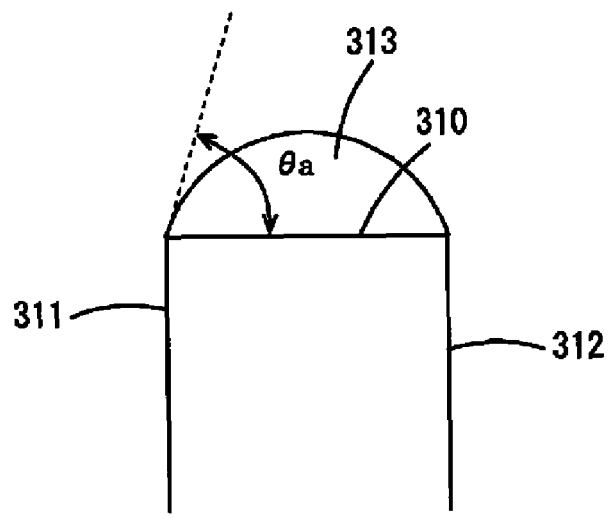
FIGS. 10(a) and 10(b) are a set of diagrams for illustrating the state where, of three solid surfaces 310, 311, and 312 arranged in a stage shape, a droplet 313 is placed on the horizontal surface 310.
Figure 10B:
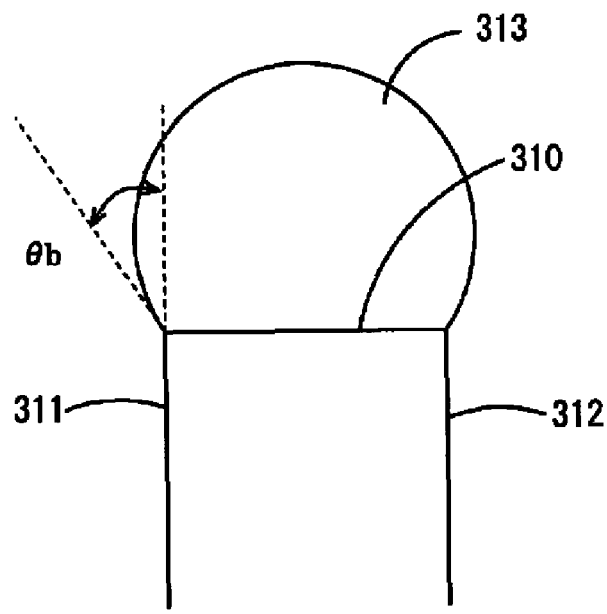

FIGS. 10(a) and 10(b) show three solid surfaces 310, 311, and 312 arranged in a stage shape and a droplet 313 placed on the horizontal surface 310.

As shown in FIG. 10(a), even if the angle θa formed by the droplet 313 and the solid surface 310 is larger than the original wetting angle between the droplet 313 and the solid surface 310, the droplet 313 cannot spread any farther so as to reduce the free energy, thus resting in that state.

As shown in FIG. 10(b), the droplet 313, placed on the horizontal solid surface 310, which is the center of the three solid surfaces 310, 311, and 312 arranged in a stage shape, does not spread until the angle θb between the surface of the droplet 313 and the solid surface 311 or 312 descending from the solid surface 31 in a substantially perpendicular direction exceeds the original wetting angle between the droplet 313 and the solid surface 311 or 312. The droplet 313 spreads onto the solid surface 311 or 312 only after the angle θb shown in FIG. 10(b) exceeds the original wetting angle between the droplet 313 and the solid surface 311 or 312.

As is obvious from the above description, the droplet 313 can be prevented from spreading by the corners between the surfaces 310 and 311 and between the surfaces 310 and 312, as shown in FIGS. 10(a) and 10(b). In addition, the droplet 313 of the aqueous solution can be more effectively prevented from spreading if the solid surface 311 or 312 descending from the horizontal solid surface 310 in a substantially perpendicular direction, which is the center of the three solid surfaces 310, 311, and 312 arranged in a stage shape, is hydrophobic.

In the probe array substrate 100 according to the present invention, based on the principle described above, the corners formed by the side surfaces of the isolating grooves 112, namely, the descending wall surfaces 113, and the main surface 101 effectively prevent the probe solutions introduced into the probe-holding portions 102 from spreading.

Thus, the probe array substrate 100 according to the present invention can eliminate the influence of spreading of the probe solutions so that the packing density of probe spots can be increased. In particular, the descending wall surfaces 113 are preferably hydrophobic because the corners formed by the descending wall surfaces 113, defined by the side surfaces of the isolating grooves 112, and the main surface 101 provide a greater effect of stopping the probe solutions from spreading if the descending wall surfaces 113 are hydrophobic.

If the probe array substrate 100 according to the present invention is used, the probe-holding portions 102, which are defined by recesses, can hold larger amounts of probe solutions than those of a normal flat substrate. Thus, relatively large amounts of probe solutions can be spotted, so that it is easy to control the amounts of probe solutions spotted and therefore to reduce variations in the amounts of probe solutions spotted.

In addition, if the probe array substrate 100 according to the present invention is used, the isolating grooves 112 can prevent the probe solutions from spreading even if they are spotted in slightly excessive amounts. Accordingly, relatively large amounts of probe solutions spotted can be set. This makes it easier to control the amounts of probe solutions spotted and therefore to reduce variations in the amounts of probe solutions spotted.

In addition, if the probe array substrate 100 according to the present invention is used, the probe molecules can also be held on the side surfaces of the probe-holding portions 102 because they are defined by recesses. This increases the number of probe molecules that can be held in the probe-holding portions 102, that is, the number of probe molecules held in the spots, thus increasing the sensitivity of the probe array.

As described above, if the probe-holding portions 102 and the isolating grooves 112 of the probe array substrate 100 are formed by dry etching or by wet etching with an alkaline liquid, an aspect ratio exceeding 20 can be achieved, and therefore a probe array substrate 100 having deep probe-holding portions 102 can be produced. That is, it is possible to increase not only the volume of the probe-holding portions 102, but also the area of the inner surfaces of the probe-holding portions 102. This enhances the advantage, described above, that the amounts of probe solutions that can be spotted can be increased and the advantage, described above, that the probe molecules can also be held on the side surfaces of the probe-holding portions 102.

If the method shown in FIG. 6 is used, as described above, the aqueous probe solutions 210 are introduced and charged into the probe-holding portions 102 of the probe array substrate 100 by the wetting force acting between the probe-holding portions 102 of the probe array substrate 100 and the aqueous probe solutions 210. The operation mechanism will be described below using FIGS. 11 to 13.

Figure 11:
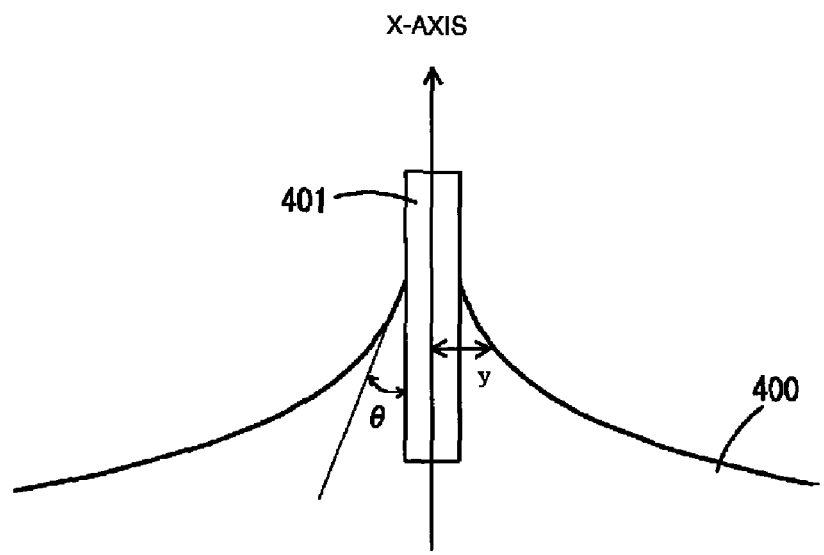
FIG. 11 is a diagram for illustrating the state where a solid cylinder 401 is perpendicularly inserted into a surface of a liquid 400.

First, a reference will be made to FIG. 11 in preparation for the description. FIG. 11 shows the state where a solid cylinder 401 is perpendicularly inserted into a surface of a liquid 400. In FIG. 11, an x-axis is set along the central axis of the cylinder 401. The surface of the liquid 400 forms a circle centered on the x-axis in a cross section taken for each x coordinate.

Letting the radius of the circle be y, the surface area S of the surface of the liquid 400 can be expressed by equation 1 below.

equation 1

$$S = \int_{x_1}^{x_2} 2\pi y \cdot \sqrt{(dx)^2 + (dy)^2}$$
$$= \int_{x_1}^{x_2} 2\pi y \cdot \sqrt{y'^2 + 1} \cdot dx$$

equation 1

The surface tension of the liquid 400 makes its surface area a minimum. In addition, there is no constraint that the liquid 400 is to be maintained at constant volume because there is a supply source for the liquid 400. Accordingly, the definite integral of equation 1 is stationary with respect to infinitesimal changes in the function form of y. Hence, the Euler differential equation represented by equation 2 below holds (see Akira Harashima, "Mechanics II—Analytical Mechanics", 21st edition, Shokabo Publishing Co., Ltd., Oct. 25, 1990, pp. 13-20).

equation 2

$$\frac{d}{dx}\frac{\partial}{\partial y'}\left(2\pi y \cdot \sqrt{y'^2+1}\right) = \frac{\partial}{\partial y}\left(2\pi y \cdot \sqrt{y'^2+1}\right)$$

equation 2

Rearranging equation 2 above gives equation 3 below.

equation 3

$$\frac{d}{dx}\left(2\pi y \cdot y' / \sqrt{y'^2+1}\right) = 2\pi \cdot \sqrt{y'^2+1}$$
$$1 + y'^2 - y \cdot y'' = 0$$

equation 3

Equation 4 below is then derived by solving the differential equation of equation 3 above.

$$y = A \cdot \cosh\{(x-B)/A\}$$ equation 4

In equation 4, A and B are arbitrary constants determined by the boundary condition. In the case in FIG. 11, for example, the boundary condition is that the cylinder 401 and the liquid 400 form an intrinsic wetting angle θ. In addition, cosh is a hyperbolic cosine function defined by equation 5 below.

$$\cosh\xi = \{\exp\xi + \exp(-\xi)\}/2$$ equation 5

If the method shown in FIG. 6 is used, when the liquid-introducing protrusions 104 formed in the probe-holding portions 102 of the probe array substrate 100 come into contact with the aqueous probe solutions 210, as the first physical step, the aqueous probe solutions 210 are guided by the liquid-introducing protrusions 104 to reach the bottom surfaces 103 of the probe-holding portions 102. Because the liquid-introducing protrusions 104 are hydrophilic, the aqueous probe solutions 210 are attracted along the guide grooves 107 and 110 of the liquid-introducing protrusions 104 (see FIG. 3) to the bottom surfaces 103 of the probe-holding portions 102 by capillarity.

Even if the liquid-introducing protrusions 104 have no guide grooves, the aqueous probe solutions 210 reach the bottom surfaces 103 of the probe-holding portions 102 if the liquid-introducing protrusions 104 are inserted deep inside the openings of the nozzles 204 formed on the silicon portion 203 of the feeder 200 until the tips of the nozzles 204 are sufficiently brought close to the bottom surfaces 103 of the probe-holding portions 102. Accordingly, the liquid-introducing protrusions 104 do not necessarily have to have guide grooves, although the liquid-introducing protrusions 104 preferably have guide grooves to attract the aqueous probe solutions 210 more reliably and smoothly onto the bottom surfaces 103 of the probe-holding portions 102.

As described above, if the liquid-introducing protrusions 104 have succeeded in guiding the aqueous probe solutions 210 to the bottom surfaces 103 of the probe-holding portions 102, as the next physical step, the aqueous probe solutions 210 must sufficiently spread over the bottom surfaces 103 of the probe-holding portions 102 to reach the inner side surfaces 111 of the probe-holding portions 102. The conditions for this physical step to be carried out will be described using FIG. 12.

Figure 12:
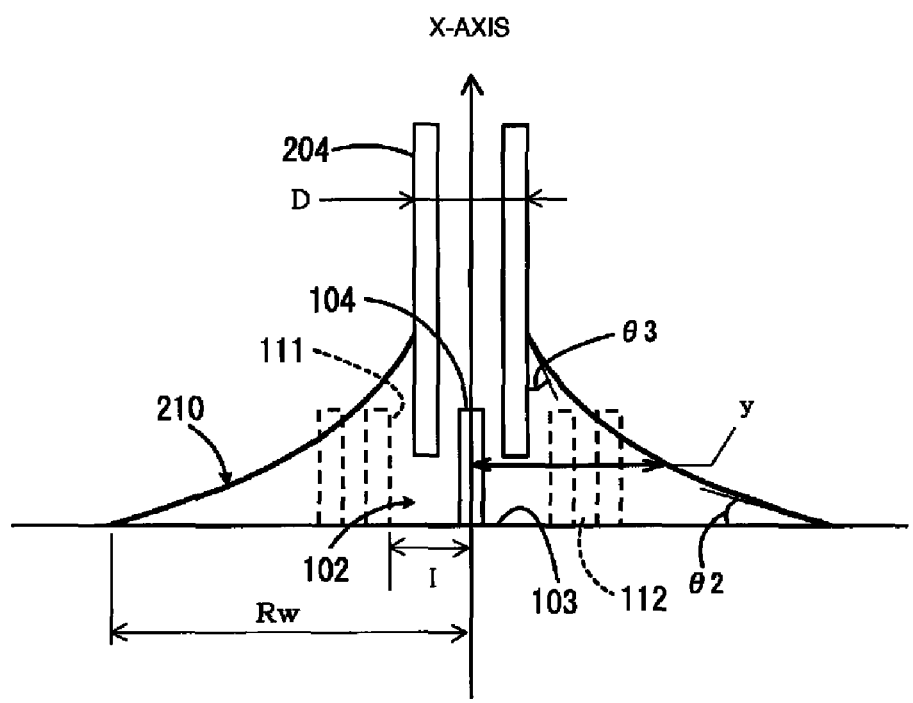
FIG. 12 is a diagram for illustrating a process in which an aqueous probe solution 210 guided to a bottom surface 103 of a probe-holding portion 102 spreads sufficiently over the bottom surface 103 of the probe-holding portion 102 to reach inner side surfaces 111 of the probe-holding portion 102.

Although in reality the probe-holding portions 102 have a finite size and have the inner side surfaces 111, the case where the probe-holding portions 102 have an infinite size and have no inner side surfaces 111 will be considered in the following discussion. In FIG. 12, the inner side surfaces 111 and so on of the probe-holding portion 102, which are actually present, are indicated by the broken lines. Under such conditions, if the amount of spread Rw of the aqueous probe solution 210 exceeds the inner side surfaces 111 of the probe-holding portion 102, it theoretically demonstrates that the aqueous probe solution 210 reaches the inner side surfaces 111 of the probe-holding portion 102.

In FIG. 12, equation 4 above holds between the radius y of the surface of the aqueous probe solution 210 and x. In addition, the probe-holding portion 102 and the aqueous probe solution 210 form an intrinsic wetting angle θ2 at the "wetting end" on the bottom surface 103 of the probe-holding portion 102. In addition, the peripheral surface of the nozzle 204 and the aqueous probe solution 210 form an intrinsic wetting angle θ3 at the "wetting end" on the peripheral surface of the nozzle 204. From these, the amount of spread Rw of the aqueous probe solution 210 is calculated by equation 6 below.

$$Rw = [D \times \cosh\{\operatorname{arcsinh}(1/\tan\theta 2)\}]/[2 \times \cosh\{\operatorname{arcsinh}(\tan\theta 3)\}]$$ equation 6 where D is the outer diameter of the nozzle 204 of the feeder 200. Accordingly, the aqueous probe solution 210 certainly reaches the inner side surfaces 111 of the probe-holding portion 102 if inequality 7 below holds, where I is the distance from the center of the liquid-introducing protrusion 104 to the inner side surfaces 111 of the probe-holding portion 102.

$$I < [D \times \cosh\{\text{arcsinh}(1/\tan\theta2)\}]/[2\times\cosh\{\text{arcsinh}(\tan\theta3)\}] \quad \text{inequality 7}$$

In reality, it is not necessarily true that the aqueous probe solution 210 does not reach the inner side surfaces 111 of the probe-holding portion 102 unless inequality 7 holds; in some cases, the aqueous probe solution 210 may spread farther than calculated along fine irregular recesses on the bottom surface of the probe-holding portion 102. Nevertheless, for the aqueous probe solution 210 to certainly reach the inner side surfaces 111 of the probe-holding portion 102, it is desirable that inequality 7 hold.

In the example described above, the distance I from the center of the liquid-introducing protrusion 104 to the inner side surfaces 111 of the probe-holding portion 102 is 35 μm, the outer diameter D of the nozzle 204 of the feeder 200 is 50 μm, and the angles θ2 and θ3, which are wetting angles between a silicon oxide film and water, are 4° to 20°. If the left and right sides of inequality 7 are calculated from these values, the left side is 35 (μm), whereas the right side, which depends on the values of θ2 and θ3 but if calculated within the range of 4° to 20°, is minimized, namely, 68 (μm), for θ2=θ3=4°, and is maximized, namely, 357 (μm), for θ2=θ3=20°. Thus, inequality 7 holds anyway. According to the example described above, therefore, the aqueous probe solution 210 certainly reaches the inner side surfaces 111 of the probe-holding portion 102.

Here the function "arcsinh" in equation 6 and inequality 7 will be described. The function "arcsinh" is an inverse function of the hyperbolic sine function "sinh". The hyperbolic sine function "sinh" is a function defined by equation 8 below.

$$\sinh\xi = \{\exp\xi - \exp(-\xi)\}/2 \quad \text{equation 8}$$

Because the surfaces of the probe-holding portion 102 are formed of a silicon oxide film and are therefore hydrophilic, the aqueous probe solution 210 reaching the inner side surfaces ill of the probe-holding portion 102 rises along the inner side surfaces 111. Consequently, the probe-holding portion 102 is filled with the aqueous probe solution 210. According to the principle of minimum free energy, it is obvious that this physical process proceeds.

After the probe-holding portion 102 is completely filled with the aqueous probe solution 210, the aqueous probe solution 210 spreads over the main surface 101 of the probe array substrate 100. Eventually, the aqueous probe solution 210 stops spreading upon reaching the isolating grooves 112, thus having the shape shown in FIG. 13. The mechanism by which the spreading is stopped is as described above using FIG. 10.

If the nozzles 204 of the silicon portion 203 of the feeder 200 have an insufficient length, the aqueous probe solutions 210 may rise along the peripheral surfaces of the nozzles 204 to reach the downward surface of the feeder 200, thus causing the risk that the aqueous probe solutions 210 are mixed between the adjacent nozzles 204. To avoid mixing of different aqueous probe solutions 210, the nozzles 204 need to be sufficiently long. The preferred length of the nozzles 204 will be discussed below.

Figure 13:
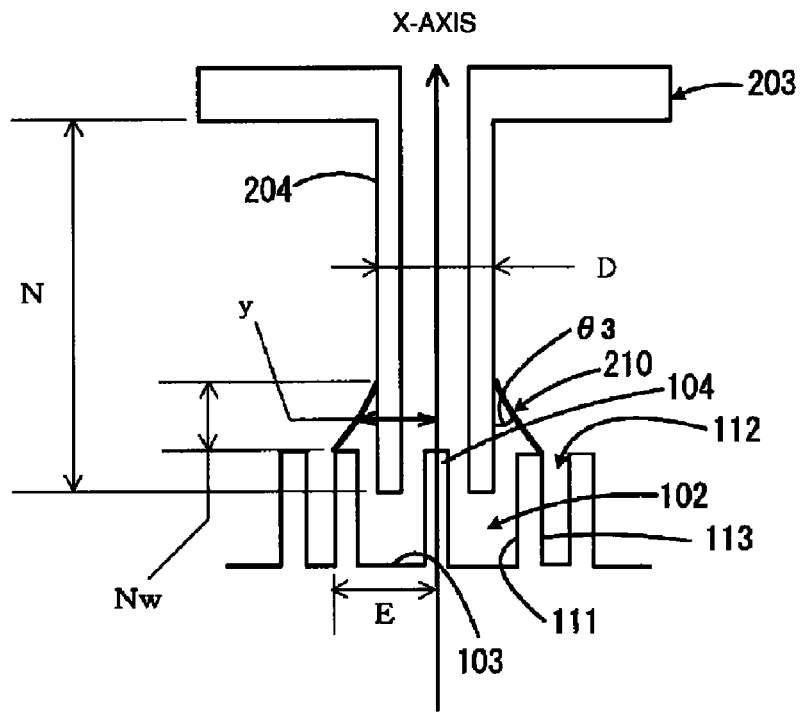
FIG. 13 is a diagram for illustrating the state where the aqueous probe solution 210 is stopped from spreading after completely filling the probe-holding portion 102, spreading over the main surface 101 of the probe array substrate 100, and reaching the isolating grooves 112.

To determine the preferred length of the nozzles 204, the amount of rise Nw in FIG. 13 may be calculated. In FIG. 13, equation 4 above holds between the radius y of the surface of the aqueous probe solution 210 and x. In addition, the peripheral surface of the nozzle 204 and the aqueous probe solution 210 form an intrinsic wetting angle θ3 at the "wetting end" on the peripheral surface of the nozzle 204. From these, Nw is calculated as in equation 9 below.

$$Nw = D \times [\text{arccosh}\{(2E/D)\times\cosh(\phi)\} - \phi]/[2\times\cosh(\phi)] \quad \text{equation 9}$$

where D is the outer diameter of the nozzle 204, and E is the distance from the center of the liquid-introducing protrusion 104 to the isolating grooves 112 (descending wall surfaces 113). Using θ3, φ is defined by equation 10 below.

$$\phi = \text{arcsinh}(\tan\theta3) \quad \text{equation 10}$$

If the length of the nozzle 204, N, is larger than the value of Nw calculated above and inequality 11 below holds, the aqueous probe solution 210 can be stopped from rising somewhere on the nozzle 204.

$$N > D \times [\text{arccosh}\{(2E/D)\times\cosh(\phi)\} - \phi]/[2\times\cosh(\phi)] \quad \text{inequality 11}$$

In the example described above, the length N of the nozzle 204 is 220 μm, the outer diameter D of the nozzle 204 is 50 μm, the distance E from the center of the liquid-introducing protrusion 104 to the isolating grooves 112 (descending wall surfaces 113) is 45 μm and the angle θ3, which is a wetting angle between a silicon oxide film and water, is 4° to 20°. These values are used to examine whether inequality 11 holds.

First, the left side of inequality 11 is 220 μm. The right side, which depends on the value of Θ3 but if calculated within the range of 4° to 20°, is maximized, namely, 28 μm, for θ3=4°, and is minimized, namely, 21 μm for θ3=20°. Thus, inequality 11 holds anyway. According to the example described above, therefore, the rising of the aqueous probe solution 210 along the peripheral surface of the nozzle 204 is stopped somewhere on the nozzle 204, thus causing little risk that different aqueous probe solutions 210 are mixed after rising onto the downward surface of the feeder 200.

The function "arccosh" in equation 9 and inequality 11 is an inverse function of the hyperbolic cosine function "cosh" defined by equation 5. Theoretically, the hyperbolic cosine function "cosh" has two possible inverse functions, although the inverse function defined as "arccosh" is a function that always gives a value of zero or more. By definition, therefore, the function "arccosh" is uniquely determined.

If a feeder having a plurality of nozzles arranged thereon, such as the feeder 200 shown, is used, it is desirable to avoid rising of the aqueous probe solutions onto the downward surface of the feeder because, as described above, it contributes to mixing of different aqueous probe solutions; therefore, it is desirable that inequality 11 hold. Even if a single nozzle is used, it is desirable that inequality 11 hold and that the nozzle be sufficiently long relative to the amount of rise of the aqueous probe solution because it is not preferable that the aqueous probe solution rises onto a portion holding and manipulating the nozzle.

In addition, it is more preferable that the peripheral surfaces of the nozzles be hydrophobic because the aqueous probe solutions can be prevented from rising. In this case, it is not necessary that the entire peripheral surfaces of the nozzles be hydrophobic; the effect of preventing excessive rising can be achieved if the nozzles are hydrophobic at least around the roots thereof while remaining hydrophilic around the tips thereof. The peripheral surfaces of the nozzles can be made hydrophobic by, for example, applying a hydrophobic liquid.

Figure 14:
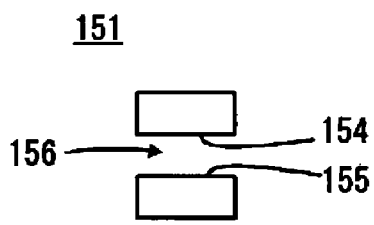
FIG. 14 is a diagram, corresponding to FIG. 3, for illustrating a second embodiment of the present invention.
Figure 15:
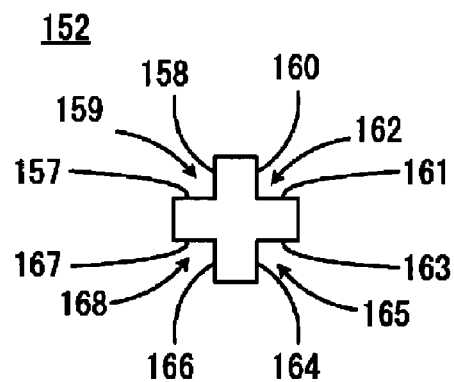
FIG. 15 is a diagram, corresponding to FIG. 3, for illustrating a third embodiment of the present invention.
Figure 16:
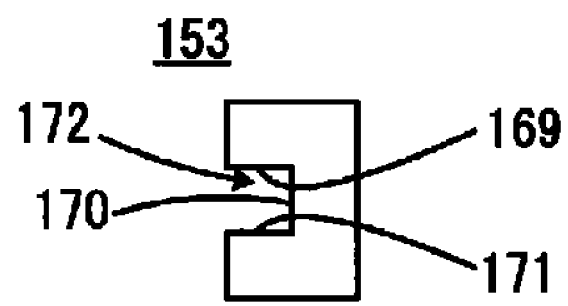
FIG. 16 is a diagram, corresponding to FIG. 3, for illustrating a fourth embodiment of the present invention.

FIGS. 14, 15, and 16 are diagrams, corresponding to FIG. 3, for illustrating second, third, and fourth embodiments, respectively, of the present invention, showing variations on liquid-introducing protrusions formed on bottom surfaces of probe-holding portions of probe array substrates.

Liquid-introducing protrusions 151, 152, and 153 shown in FIGS. 14, 15, and 16, respectively, have guide grooves for smoothly introducing probe solutions into probe-holding portions.

The liquid-introducing protrusion 151 shown in FIG. 14 has a guide groove 156 defined between surfaces 154 and 155 extending parallel to each other.

The liquid-introducing protrusion 152 shown in FIG. 15 has a guide groove 159 having an L-shaped cross section defined by surfaces 157 and 158, a guide groove 162 having an L-shaped cross section defined by surface 160 and 161, a guide groove 165 having an L-shaped cross section defined by surfaces 163 and 164, and a guide groove 168 having an L-shaped cross section defined by surfaces 166 and 167.

The liquid-introducing protrusion 153 shown in FIG. 16 has a guide groove 172 having a rectangular cross section defined by three surfaces 169, 170, and 171 sequentially extending in perpendicular directions.

The invention claimed is:

1. A probe array substrate comprising:
a substrate having a main surface and a plurality of probe-holding portions arranged along the main surface; and
a plurality of walls descending in a substantially perpendicular direction from the main surface, inner surfaces of each of the plurality of the walls defining a respective probe-holding portion of the plurality of probe-holding portions, outer surfaces of each of the plurality of the walls defining a recess between adjacent probe-holding portions of the plurality of probe holding portions,
wherein the inner surfaces of each of the plurality of the walls are hydrophilic and the outer surfaces of each of the plurality of walls are hydrophobic.

2. The probe array substrate according to claim 1, wherein isolating grooves are located between the adjacent probe-holding portions.

3. The probe array substrate according to claim 1, further comprising liquid-introducing protrusions in the probe-holding portions.

4. The probe array substrate according to claim 3, wherein the liquid-introducing protrusions have guide grooves for introducing probe solutions into the probe-holding portions.

5. The probe array substrate according to claim 4, wherein the guide grooves are located between parallel surfaces of the liquid-introducing protrusions.

6. The probe array substrate according to claim 4, wherein the liquid-introducing protrusions have at least two guide grooves.

7. The probe array substrate according to claim 6, wherein the liquid-introducing protrusions have four guide grooves.

8. The probe array substrate according to claim 4, wherein the guide grooves have an L-shaped cross-section.

9. The probe array substrate according to claim 4, wherein the guide grooves have a rectangular cross-section.

10. A probe array comprising the probe array substrate according to claim 1 and probe molecules held in the individual probe-holding portions of the probe array substrate.

11. A method for producing a probe array substrate having a main surface and a plurality of probe-holding portions arranged along the main surface, the method comprising:
preparing a material substrate to be the probe array substrate;
forming a plurality of walls descending in a substantially perpendicular direction from a main surface of the material substrate, inner surfaces of each of the plurality of the walls defining a respective probe-holding portion of the plurality of probe-holding portions, outer surfaces of each of the plurality of the walls defining a recess between adjacent probe-holding portions of the plurality of probe-holding portions;
making the inner surfaces each of the plurality of the walls hydrophilic; and
making the outer surfaces of each of the plurality of walls hydrophobic.

12. The method for producing a probe array substrate according to claim 11, wherein the inner surfaces and outer surfaces of the plurality of walls are formed simultaneously.

13. The method for producing a probe array substrate according to claim 12, wherein the material substrate is formed of silicon and the step of forming the plurality of walls is carried out by dry etching.

14. The method for producing a probe array substrate according to claim 12, wherein the material substrate is a monocrystalline silicon substrate whose main surface is a (110) crystal plane wherein the outer surfaces and the inner surfaces are (111) crystal planes, and the step of forming the plurality of walls is carried by wet etching with an alkaline liquid.

15. A method for producing a probe array, comprising the steps of:
preparing the probe array substrate according to claim 3;
preparing nozzles charged with probe solutions; and
guiding the probe solutions into the probe-holding portions of the probe array substrate by bringing the nozzles close to the liquid-introducing protrusions formed in the probe-holding portions so that the probe solutions come into contact with the liquid-introducing protrusions.

16. The method for producing a probe array according to claim 15, wherein:

$$I < [D \times \cosh\{\arcsinh(1/\tan\theta 2)\}]/[2 \times \cosh\{\arcsinh(\tan\theta 3)\}]$$

wherein
D is an outer diameter of the nozzles;
I is a distance between inner side surfaces of the probe-holding portions and the liquid-introducing protrusions;
θ2 is a wetting angle between the main surface of the probe array substrate and the probe solutions around the probe-holding portions; and
θ3 is a wetting angle between peripheral surfaces of the nozzles and the probe solutions.

17. The method for producing a probe array according to claim 15, wherein:

$$N > D \times [\arccos\{(2E/D) \times \cosh(\phi)\} - \phi]/[2 \times \cosh(\phi)]$$

wherein
D is an outer diameter of the nozzles;
N is a length of the nozzles;
E is a distance from centers of the liquid-introducing protrusions to the descending wall surfaces;
θ3 is a wetting angle between peripheral surfaces of the nozzles and the probe solutions; and
φ is defined as φ=arcsinh(tan θ3).

18. The method for producing a probe array according to claim 15, wherein peripheral surfaces of the nozzles are at least partially hydrophobic.

19. The method for producing a probe array according to claim 15, further comprising a step of preparing a feeder having the nozzles arranged thereon,
wherein the step of guiding the probe solutions into the probe-holding portions includes a step of simultaneously introducing the probe solutions into the probe-holding portions by bringing the feeder close to the probe array substrate so that the probe solutions come into contact with the liquid-introducing protrusions.

* * * * *